United States Patent
Morioka et al.

(10) Patent No.: US 7,476,465 B2
(45) Date of Patent: Jan. 13, 2009

(54) ELECTRODE ACTIVE MATERIAL AND ELECTRODE USING THE ELECTRODE ACTIVE MATERIAL AND BATTERY USING THE ELECTRODE

(75) Inventors: Yukiko Morioka, Tokyo (JP); Masahiro Suguro, Tokyo (JP); Kentaro Nakahara, Tokyo (JP); Jiro Iriyama, Tokyo (JP); Shigeyuki Iwasa, Tokyo (JP); Masaharu Satoh, Tokyo (JP)

(73) Assignee: NEC Corporation, Tokyo (JP)

( * ) Notice: Subject to any disclaimer, the term of this patent is extended or adjusted under 35 U.S.C. 154(b) by 330 days.

(21) Appl. No.: 10/504,916

(22) PCT Filed: Feb. 18, 2003

(86) PCT No.: PCT/JP03/01733

§ 371 (c)(1),
(2), (4) Date: Aug. 18, 2004

(87) PCT Pub. No.: WO03/069703

PCT Pub. Date: Aug. 21, 2003

(65) Prior Publication Data

US 2005/0100787 A1    May 12, 2005

(30) Foreign Application Priority Data

Feb. 18, 2002    (JP) .............................. 2002-040294

(51) Int. Cl.
*H01M 4/60*    (2006.01)
*C07D 241/36*    (2006.01)
*C08G 73/06*    (2006.01)

(52) U.S. Cl. ...................... 429/213; 528/423; 544/337; 544/338; 544/343; 544/344; 544/349

(58) Field of Classification Search ................ 429/212, 429/213, 214, 215, 216, 217; 544/337, 338, 544/339, 342, 343, 344, 349; 528/423
See application file for complete search history.

(56) References Cited

U.S. PATENT DOCUMENTS 3,553,208 A * 1/1971 Abushanab ............. 544/344 X (Continued)

FOREIGN PATENT DOCUMENTS

| JP | 9-3171 | 1/1997 |
|---|---|---|
| JP | 2715778 | 11/1997 |
| JP | 2003-17062 | 1/2003 |

OTHER PUBLICATIONS

Computer-generated translation of JP 09-3171 (Yamamoto), from the Japanese Patent Office website (doc date Jan. 1997).*

Primary Examiner—Stephen J. Kalafut
(74) Attorney, Agent, or Firm—McGinn IP Law Group, PLLC

(57) ABSTRACT

An object of the present invention is to provide a battery which is high in capacity density and superior in stability. An electrode containing a compound having a diazine-N,N'-dioxide structure shown by a general formula (1) described below as an electrode active material is used, (1)

where x, y, x', and y' independently shows integer numbers of 0 or more respectively, and the order of condensation of diazine rings and benzene rings may be alternate or random. One of substituents $R_1$, $R_2$, $R_3$, $R_4$, $R_a$, $R_b$, $R_c$, and $R_d$ shows a part of main chain or side chain of oligomer or polymer, and the other independently shows hydrogen atom, halogen atom, or a specific group.

37 Claims, 1 Drawing Sheet

U.S. PATENT DOCUMENTS

| | | | |
|---|---|---|---|
| 3,567,728 A * | 3/1971 | Johnston et al. | 544/343 |
| 3,594,381 A * | 7/1971 | Seng et al. | 544/343 |
| 3,594,382 A * | 7/1971 | Seng et al. | 544/343 X |
| 3,900,473 A * | 8/1975 | Diel et al. | 544/344 X |
| 4,442,187 A | 4/1984 | MacDiarmid et al. | 429/213 |
| 4,833,048 A | 5/1989 | Dejonghe et al. | 429/104 |
| 7,018,738 B2 * | 3/2006 | Morioka et al. | 429/213 |

* cited by examiner

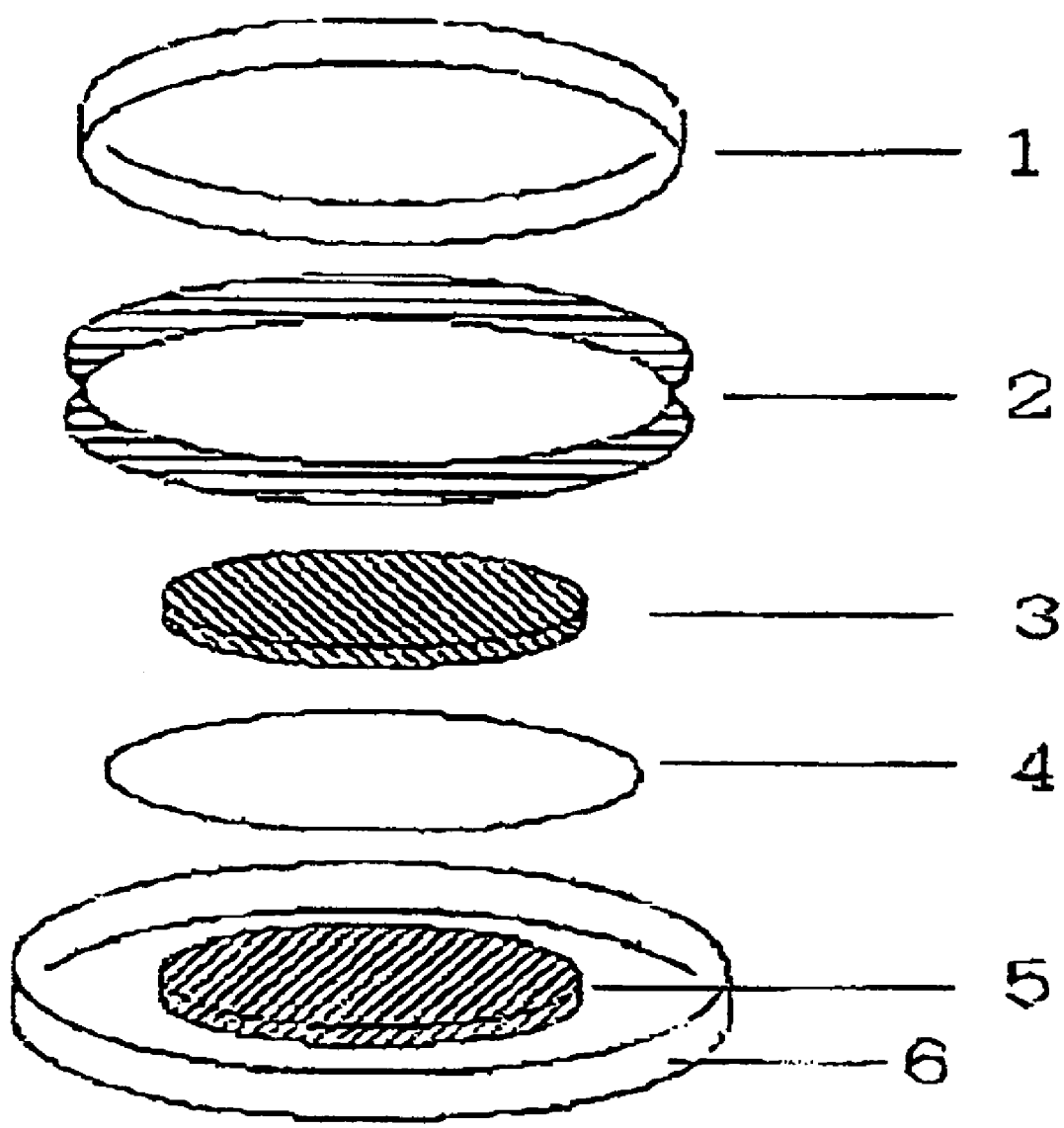

ELECTRODE ACTIVE MATERIAL AND ELECTRODE USING THE ELECTRODE ACTIVE MATERIAL AND BATTERY USING THE ELECTRODE

TECHNICAL FIELD

The present invention relates to an electrode active material and an electrode using the electrode active material as well as a battery using the electrode.

BACKGROUND OF THE ART

A battery converts chemical energy into electrical energy using redox reaction in a positive electrode and a negative electrode to extract the electrical energy or converts the electrical energy into the chemical energy to store the chemical energy and is used as a power supply in a variety of devices.

In late years, a battery with high capacity density has increasingly been required along with a rapid permeation of portable electronics devices. In order to meet the demand, a battery using alkali metal ion with a low mass per unit charge has been developed. Among these, a battery using lithium ion has particularly been utilized. Such lithium ion battery uses a lithium-containing heavy metal oxide and a carbon material as an active material of a positive electrode and a negative electrode, respectively and performs charge and discharge of the battery using an insertion reaction and a elimination reaction of lithium ion against these active material.

Such lithium ion battery however uses a heavy metal compound with a high specific gravity particularly as an active material of the positive electrode. Therefore, it is difficult to sufficiently increase a battery capacity per unit mass, so that there has been a problem of difficulty in acting as the battery with a high capacity density for the lithium ion battery.

Consequently, there has been taken an approach to develop a large capacity battery using a more lightweight electrode material. For instance, U.S. Pat. No. 4,833,048 specification and Japanese Patent Publication No.2,715,778 disclose a battery utilizing an electrochemical redox reaction on the basis of production and dissociation of a disulfide bond by means of the use of an organic compound having the disulfide bond as an active material of a positive electrode.

The battery however uses the organic compound consisting of low-mass elements such as sulfur and carbon as an electrode material. Therefore, an effect is obtained for a configuration of a battery with a high capacity density to some extent, and however recombination efficiency of dissociated disulfide bond is low, so that the battery has had a problem of insufficiency in stability of charge and discharge.

A battery using a conductive polymer as an electrode material is also disclosed as a battery using an organic compound as an active material. The battery performs charge and discharge by a doping reaction and dedoping reaction of an electrolytic ion against the conductive polymer, where the doping reaction is defined as a reaction to stabilize by counterion an exciton such as a charged soliton and polaron generated by an electrochemical redox reaction of the conductive polymer and on the other hand, the dedoping reaction is defined as a reverse reaction of the doping reaction, namely a reaction to electrochemically oxidize or reduce the exciton stabilized by the counterion.

U.S. Pat. No. 4,442,187 specification discloses a battery with a positive electrode or a negative electrode consisting of such conductive polymer. The conductive polymer is composed of low-mass elements such as carbon and nitrogen, so that the battery was highly attractive as a battery with a high capacity density.

However in general, the conductive polymer has a behavior that excitons generated by an electrochemical redox reaction are delocalized in wide-ranging areas of conjugated π-electron systems to interact each other. For this reason, there has been a problem that concentration of the generated excitons is limited so that capacity of the battery is restricted. Therefore, the battery whose electrode material is such conductive polymer has been still insufficient in capacity density growth.

DISCLOSURE OF THE INVENTION

In order to solve the problem in consideration of the circumstance, the present invention provides an electrode active material which is high in energy density and excellent in stability in charge and discharge and an electrode using the electrode active material as well as a battery using the electrode.

The present invention provides the electrode active material including a compound with a diazine-N,N'-dioxide structure which contains at least one monovalent group with a bond instead of a substituent among substituents $R_1$, $R_2$, $R_3$, $R_4$, $R_a$, $R_b$, $R_c$, and $R_d$ in the compound shown by an undermentioned general formula (1).

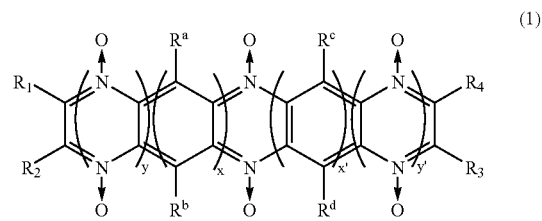

x, y, x', and y' in the above-mentioned general formula (1) independently show integer numbers of 0 or more, respectively. The order of condensation of diazine ring and benzene ring may be alternate or random. One of the substituents $R_1$, $R_2$, $R_3$, $R_4$, $R_a$, $R_b$, $R_c$, and $R_d$ shows the above-mentioned bond and the other of them independently show hydrogen atom, halogen atom, hydroxyl group, nitro group, nitroso group, cyano group, carboxyl group, substituted or unsubstituted alkyl group, substituted or unsubstituted alkenyl group, substituted or unsubstituted cycloalkyl group, substituted or unsubstituted aromatic hydrocarbon group, substituted or unsubstituted heteroaromatic group, substituted or unsubstituted aralkyl group, substituted or unsubstituted amino group, substituted or unsubstituted alkoxy group, substituted or unsubstituted allyloxy group, substituted or unsubstituted alkoxycarbonyl group, substituted or unsubstituted acyl group, substituted or unsubstituted acyloxy group. When x is 2 or more, $R_a$ on each benzene ring is not necessarily required to be same, and similarly $R_b$ on each benzene ring is not necessarily required to be same. When x' is 2 or more, $R_c$ on each benzene ring is not necessarily required to be same, and similarly $R_d$ on each benzene ring is not necessarily required to be same. One or more atom of these substituents may be replaced with sulfur atom, silicon atom, phosphor atom, or boron atom, and a ring structure may be formed with inter-substituents.

It is preferable that the compound is substantially insoluble in electrolyte. Typically, it is preferable that the compound is substantially insoluble in electrolytic solution and has molecular weight capable of maintaining the form.

The compound may be an oligomer or a polymer compound having constituent element of a diazine-N,N'-dioxide structure shown by the general formula (1) as a side chain, where for instance, oligomer is molecular weight of a level of 200 to 1000 and polymer is molecular weight of a level of 1000 to 500000. Oligomer or polymer compound is preferably copolymer.

The compound may have a structure in which coupled by connector group A shown by the undermentioned general formula (9) instead of the oligomer or polymer compound,

$$A\text{-}(B)_z \qquad (9)$$

where A shows a connector group which is a group having a single bond and an unsaturated bond, B shows monovalent group which is the general formula (1), and z is an integer number of 2 or more. Typically, in the general formula (9), z is an integer number of 2 to 10 and the connector group A comprises a substituent with z valence in which z hydrogens in an aromatic compound with 5 to 14 carbons are replaced by bonds or a divalent group including alkyne.

In addition, in the present invention, a term "connector group" is a group forming a single bond with a plurality of monovalent groups shown by the general formula (1) and means a group forming a structure different from the polymer.

The present invention also provides an electrode active material containing oligomer or polymer, wherein the oligomer or polymer is formed by polymerizing monomers including at least one monovalent group with a bond instead of one of substituents $R_1$, $R_2$, $R_3$, $R_4$, $R_a$, $R_b$, $R_c$, and $R_d$ of the compound having a diazine-N,N'-dioxide structure, which is shown by the general formula (1).

The present invention also provides an electrode containing the compound having the diazine-N,N'-dioxide structure as a reactant, reaction product, or intermediate product in at least discharge reaction of an electrode reaction.

The present invention also provides a battery having the electrode as at least one electrode among a positive electrode or a negative electrode.

The present invention further provides a battery having the electrode as a positive electrode.

The present invention also provides a secondary battery having the electrode as at least one electrode among a positive electrode or a negative electrode.

The present invention also provides a secondary battery having the electrode as a positive electrode.

The present invention also provides a lithium secondary battery having the electrode as at least one electrode among a positive electrode or a negative electrode.

The present invention also provides a lithium secondary battery having the electrode as a positive electrode.

The findings in keen examinations by inventors of the present invention reveal that in spite of a compound consisting of only low-mass element, a specific organic compound which has not been utilized as an active material of an electrode before, namely a compound with a specific diazine-N,N'-dioxide structure can be used as the active material of the electrode.

The present invention can provide an electrode which is lightweight and high capacity density and functions stably when charge and discharge, by containing the compound having such a specific diazine-N,N'-dioxide structure.

Copolymerized oligomer or copolymer of the compound having the diazine-N,N'-dioxide structure is contained as the active material in the electrode, thereby enabling to provide an electrode functioning stably when the charge and discharge. The battery is further constituted using the electrode, thereby enabling to obtain a battery with a high capacity density.

The electrode is also used as a battery for the secondary battery or lithium secondary battery, thereby enabling to provide the secondary battery or the lithium secondary battery with a high energy density.

BRIEF DESCRIPTION OF DRAWINGS

FIG. 1 is an explanatory view showing an example of a constitution of an battery of the present invention.

BEST MODES FOR CARRYING OUT THE INVENTION

FIG. 1 shows a constitution of a battery of an embodiment according to the present invention. The battery shown in FIG. 1 has a constitution in which a positive electrode 5 and a negative electrode 3 are overlapped so as to oppose each other via a separator 4 containing an electrolyte. The positive electrode 5 is arranged on a positive electrode collector 6 and the negative electrode 3 is arranged on a negative electrode collector 1, and further an insulative packing 2 made of insulative material such as plastic resin, which is a flame shape surrounding a periphery of the positive electrode, the negative electrode, and the separator, is arranged between the negative electrode collector 1 and the positive electrode collector 6 in order to prevent both collectors from electrical contact. In addition, if a solid electrolyte and a gel electrolyte are used, these electrolytes may be sandwiched between the electrodes instead of the separator.

In the present embodiment, a compound having the diazine-N,N'-dioxide structure shown by the general formula (1) as an active material used for the negative electrode 3, the positive electrode 5, or both of them. The compound may be an oligomer or polymer compound (hereinafter referred to the compound as "oligomer or polymer compound having a diazine-N,N'-dioxide structure") having a constituent element of the diazine-N,N'-dioxide structure shown by the general formula (1) as a side chain, or instead of this, may have the diazine-N,N'-dioxide structure coupled with a connector group A shown by the general formula (9).

The active material of the electrode in the present invention means a substance which makes a direct contribution to electrode reactions such as charge reaction and discharge reaction and which plays a leading role in a battery system.

The oligomer or polymer compound having the diazine-N,N'-dioxide structure as the side chain, which is used as an indispensable active material in the present invention, means an oligomer or polymer compound having a constituent element containing at least one monovalent group which has a bond in a ring of the diazine-N,N'-dioxide compound shown by the general formula (1).

A battery in the present invention preferably has a positive electrode containing a compound having a diazine-N,N'-dioxide structure as a positive electrode active material and is a lithium secondary battery containing lithium ion as electrolytic cation.

As halogen atoms of substituents of $R_1$, $R_2$, $R_3$, $R_4$, $R_a$, $R_b$, $R_c$, and $R_d$ in the general formula (1), for instance, fluorine, chlorine, bromine, iodine and so on are listed and a single group of them may be independently used or two or more groups may be combined.

As substituted or unsubstituted alkyl group, for instance, methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group and so on are listed and a single group of them may be independently used or two or more groups may be combined.

As substituted or unsubstituted alkenyl group, for instance, vinyl group, allyl group, 1-butenyl group, 2-butenyl group, 3-butenyl group, 1,3-butanedienyl group, 1-methylvinyl group, styryl group, 2,2-diphenylvinyl group, 1,2-diphenylvinyl group, 2-methylallyl group, 1,1- dimethylallyl group, 2-methylallyl group, 1-phenylallyl group, 2-phenylallyl group, 3-phenylallyl group, 3,3-diphenylallyl group, 1,2-dimethylallyl group, 1-phenyl-1-butenyl group, 3-phenyl-1-butenyl group and so on are listed and a single group of them may be independently used or two or more groups may be combined.

As substituted or unsubstituted cycloalkyl group, for instance, cyclopropyl group, cyclobutyl group, cyclopentyl group, cyclohexyl group, 4-methylcyclohexyl group and so on are listed and a single group of them may be independently used or two or more groups may be combined.

As substituted or unsubstituted aromatic hydrocarbon group, for instance, phenyl group, 1-naphthyl group, 2-naphthyl group, 9-fluorenyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthaccnyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-thryl group, m-thryl group, p-thryl group, p-t-butylphenyl group, p-(2-phenylpropyl)phenyl group, 3-methyl-2-naphtyl group, 4-methyl-1-naphtyl group, 4-methyl-1-anthryl group, 4'-methylbipbenylyl group, 4''-t-butyl-terphenyl-4-yl group, derivatives thereof and so on are listed and a single group of them may be independently used or two or more groups may be combined.

As substituted or unsubstituted heteroaromatic group, for instance, 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalynyl group, 5-quinoxalynyl group, 6-quinoxalynyl group, 1-carbazolyl group, 2-carbazolyl group, 3-carbazolyl group, 4-carbazolyl group, 9-carbazolyl group, 1-phenanthridinyl group 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acrydinyl group, 2-acrydinyl group, 3-acrydinyl group, 4-acrydinyl group, 9-acrydinyl group, 1,7-phenanthrorine-2-yl group, 1,7-phenanthrorine-3-yl group, 1,7-phenanthrorine-4-yl group, 1,7-phenanthrorine-5-yl group, 1,7-phenanthrorine-6-yl group, 1,7-phenanthrorine-8-yl group, 1,7-phenanthrorine-9-yl group, 1,7-phenanthrorine-10-yl group, 1,8-phenanthrorine-2-yl group, 1,8-phenanthrorine-3-yl group, 1,8-phenanthrorine-4-yl group, 1,8-phenanthrorine-5-yl group, 1,8-phenanthrorine-6-yl group, 1,8-phenanthrorine-7-yl group, 1,8-phenanthrorine-9-yl group, 1,8-phenanthrorine-10-yl group, 1,9-phenanthrorine-2-yl group, 1,9-phenanthrorine-3-yl group, 1,9-phenanthrorine-4-yl group, 1,9-phenanthrorine-5-yl group, 1,9-phenanthrorine-6-yl group, 1,9-phenanthrorine-7-yl group, 1,9-phenanthrorine-8-yl group, 1,9-phenanthrorine-10-yl group, 1,10-phenanthrorine-2-yl group, 1,10-phenanthrorine-3-yl group, 1,10-phenanthrorine-4-yl group, 1,10-phenanthrorine-5-yl group, 2,9-phenanthrorine-1-yl group, 2,9-phenanthrorine-3-yl group, 2,9-phenanthrorine-4-yl group, 2,9-phenanthrorine-5-yl group, 2,9-phenanthrorine-6-yl group, 2,9-phenanthrorine-7-yl group, 2,9-phenanthrorine-8-yl group, 2,9-phenanthrorine-10yl group, 2,8-phenanthrorine-1-yl group, 2,8-phenanthrorine-3-yl group, 2,8-phenanthrorine-4-yl group, 2,8-phenanthrorine-5-yl group, 2,8-phenanthrorine-6-yl group, 2,8-phenanthrorine-7-yl group, 2,8-phenanthrorine-9-yl group, 2,8-phenanthrorine-10-yl group, 2,7-phenanthrorine-1-yl group, 2,7-phenanthrorine-3-yl group, 2,7-phenanthrorine-4-yl group, 2,7-phenanthrorine-5-yl group, 2,7-phenanthrorine-6-yl group, 2,7-phenanthrorine-8-yl group, 2,7-phenanthrorine-9-yl group, 2,7-phenanthrorine-10-yl group, 1-phenadinyl group, 2-phenadinyl group, 1-phenanthridinyl group, 2-phenothiadinyl group, 3-phenothiadinyl group, 4-phenothiadinyl group, 10-phenothiadinyl group, 1-phenoxadinyl group, 2-phenoxadinyl group, 3-phenoxadinyl group, 4-phenoxadinyl group, 10-phenoxadinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-buty)-3-indolyl group, and derivatives thereof and so on are listed and a single group of them may be independently used or two or more groups may be combined.

As substituted or unsubstituted aralkyl group, for instance, benzyl group, 1-phenylethyl group, 2-phenylethyl group, 1-phenylisopropyl group, 2-phenylisopropyl group, 2-phenylisopropyl group, phenyl-t-butyl-group, α-naphthylmethyl group, 1-α-naphthylethyl group, 2-α-naphthylethyl group, 1-α-naphthylisopropyl group, 2-α-naphthylisopropyl group, β-naphthylmethyl group, 1-βnaphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, 1-chloro-2-phenylisopropyl group and so on are listed and a single group of them may be independently used or two or more groups may be combined.

A substituted or unsubstituted amino group is also expressed by —$NX^1X^2$, and as the substituent $X^1$ and $X_2$ independently, for instance, hydrogen atom, the above-mentioned substituted or unsubstituted alkyl group, the substituted or unsubstituted alkenyl group, the substituted or unsubstituted cycloalkyl group, the substituted or unsubstituted aromatic hydrocarbon group, the substituted or unsubstituted heteroaromatic group, the substituted or unsubstituted aralkyl group and so on are listed and a single group of them may be independently used or two or more groups may be combined.

The substituted or unsubstituted alkoxy group and the substituted or unsubstituted alkoxycarbonyl group are expressed by —$OX^3$ and —$COOX^4$, and as the substituents $X^3$ and $X^4$ respectively, for instance, the above-mentioned substituted or unsubstituted alkyl group, the substituted or unsubstituted cycloalkyl group, and the substituted or unsubstituted aralkyl group and so on are listed, and a single group of them may be independently used or two or more groups may be combined.

The substituted or unsubstituted alkoxy group and the substituted or unsubstituted alkoxycarbonyl group are also expressed by —$OX^3$ and —$COOX^4$, and as the substituents $X^3$ and $X^4$ respectively, for instance, the above-mentioned substituted or unsubstituted alkyl group, the substituted or unsubstituted cycloalkyl group, and the substituted or unsubstituted aralkyl group and so on are listed, and a single group of them may be independently used or two or more groups may be combined.

The substituted or unsubstituted allyloxy group and the substituted or unsubstituted allyloxycarbonyl group are also expressed by —$OX^5$ and —$COOX^6$ respectively, and as substituents $X^5$ and $X^6$, for instance, the above-mentioned substituted or unsubstituted aromatic hydrocarbon group, substituted or unsubstituted heteroaromatic group and so on are listed and a single group of them may be independently used or two or more groups may be combined.

The substituted or unsubstituted acyl group and the substituted or unsubstituted acyloxy group are also expressed by —$C(=O)X^7$ and —$OC(=)X^8$ respectively, and as substituents $X^7$ and $X^8$, for instance, hydrogen atom, the above-mentioned substituted or unsubstituted alkyl group, the substituted or unsubstituted alkenyl group the substituted or unsubstituted cycloalkyl group, the substituted or unsubstituted aromatic hydrocarbon group, the substituted or unsubstituted heteroaromatic group, the substituted or unsubstituted aralkyl group and so on are listed and a single group of them may be independently used or two or more groups may be combined.

Also an examples of divalent group forming a ring, tetramethylene group, pentamethylene group, hexamethylene group, diphenylmethane-2,2-diyl group, diphenylethane-3, 3'-diyl group, diphenylpropane-4,4-diyl group, 1,3-butadiene-1,4-diyl group, derivatives thereof and so on are listed.

At least one atoms of the above-mentioned substituents may also be substituted by sulfur atom, silicon atom, phosphor atom, or boron atom. As groups substituted by sulfur atom, for instance, substituents in which sulfur atom is substituted for oxygen atom of oxygen-containing group such as hydroxyl group, carboxyl group, alkoxy group, alkoxycarbonyl group, allyloxy group, allyloxycarbonyl group, acyl group, acyloxy group may be listed. As examples of the substituents, mercaptol group, dithiocarboxyl group, hydroxy(thiocarbonyl) group, mercaptolcarbonyl group, methylthio group, methoxythiocarbonyl group, methylthiocarbonyl group, methyldithiocarboxyl group, phenylthio group, phenoxythiocarbonyl group, phenylthiocarbonyl group, phenyldithiocarbonyl group, methylthiocarbonyl group, phenylthiocarbonyl group and so on are listed. As groups substituted with silicon atom, for instance, substituents in which silicon atom is substituted for carbon atom of the above-mentioned alkyl group, alkenyl group, cycloalkyl group, and aralkyl group are listed. As examples of the substituents, silyl group, methylsilyl group, silylmethyl group, ethylsilyl group, (methylsilyl)methyl group, dimethylsilyl group, trimethylsilyl group, t-butyldimethylsilyl group, triisopropylsilyl group and SO on are listed. As groups substituted with phosphor atom, for instance, substituents in which phosphor atom is substituted for nitrogen atom of the above-mentioned amino group. As examples of the substituents, phosphino group, trimethylphosphino group, triphenylphosphino group and so on are listed. As groups substituted with boron atom, for instance, substituents in which phosphor atom is substituted for nitrogen atom of the above-mentioned amino group are listed. As examples of the substituents, dimethylboryl group, diphenylboryl group and so on are listed.

As examples of the aromatic compound of connector group A in the general formula (9), benzene, naphthalene, azulene, biphenylene, indacene, acenaphthylene, anthracene, thiophene, thianthrene, furan, pyran, pyrrole, pyridine, pyrazine, pyrimidine, pyridadine, triazine, indole, quinoline, isoquinoline, phthalazine, naphthyridine, quinoxaline, carbazole, phenanthridine, acridine, phenazine, phenanthroline, phenoxazine and so on are listed.

As examples of divalent group including alkyne of the connector group A in the general formula (9), ethynylene group and butadienylene group are listed.

In addition, compound having diazine-N,N'-dioxide structure coupled through the connector group A in the present invention may be manufactured through known synthetic method of coupling the corresponding diazine derivative with a given connector group and followed by carrying out oxidization and the like.

The compound having diazine-N,N'-dioxide structure in the present invention performs as an electrode active material in an electrode, and is contained as reactant, reaction product, or intermediate product in the electrode in discharge reaction of electrode reaction or in discharge reaction and charge reaction. Diazine-N,N'-dioxide ring in the compound having the diazine-N,N'-dioxide structure is considered to have a redox reaction shown by a reaction formula (A) described below as the electrode equation, where reaction formula (A) shows only diazine-N,N'-dioxide ring part.

The oligomer or polymer compound having the diazine-N,N'-dioxide structure as the side chain in the present invention is preferably low in the solubility into the electrolytic solution as described above. If molecular weight is too large, diazine ring is hard to be oxidized and refinement is difficult, resulting in possibility of reduction of capacity. Therefore, molecular weight is desirably within the above-mentioned range.

As specific examples of oligomer or polymer compound having the diazine-N,N'-dioxide structure as the side chain in the present invention, compounds expressed by chemical formulas (2) to (8) below are listed, however the present invention is not limited to these as long as the aforementioned main point is not exceeded.

Reaction Formula (A)

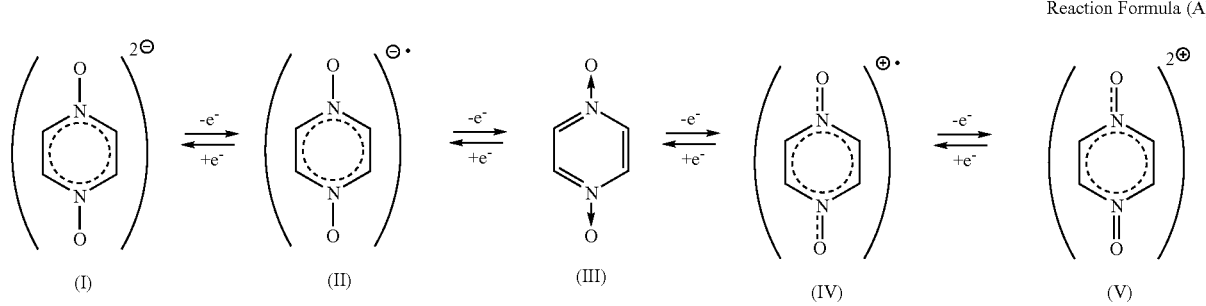

In particular, it is desirable to use one-electron redox reaction between compound (III) and compound (IV) of the reaction formula (A), one-electron redox reaction between the compound (III) and compound (II), two-electron redox reaction between the compound (II) and the compound (IV).

Oligomer or polymer compound having the diazine-N,N'-dioxide structure as a side chain in the present invention may be a homopolymer formed through polymerization of only monomer having the diazine-N,N'-dioxide structure as the side chain or may be copolymer formed together with other monomer.

The compound having the diazine-N,N'-dioxide structure in the present invention is preferably as low as possible in solubility to electrolytic solution, that is, poor solubility or insolubility is preferable. The solubility of the compound in the electrolytic solution, for instance, in 100 g of solvent for electrolytic solution such as propylene carbonate, is 1 g or less, more preferably 0.5 g or less, further more preferably 0.1 g or less.

Molecular weight of the compound having diazine-N,N'-dioxide structure is preferably large from a viewpoint of the solubility into the electrolytic solution, however a diazine bone structure shown by the general formula (1) is preferably $x+y+x'+y' \leq 20$ from a viewpoint of the solubility into reaction solvent in manufacturing, more preferably $x+y+x'+y' \leq 10$. Weight-average molecular weight of oligomer or polymer (standard sample: polystyrene) through gel permeation chromatography (GPC) is preferably 200,000 or less, more preferably 100,000 or less.

The oligomer or polymer compound having the diazine-N,N'-dioxide structure as the side chain in the present invention may be manufactured through the known synthetic method in which olefin substituted with the corresponding diazine derivative is subjected to, for instance, free-radical polymerization to form oligomer or polymer, and oxidize the same using peroxide or peracid. For instance, poly (2-vinylpyrazine-N,N'-dioxide) synthetic method is described in Iranian Journal of Science & Technology, page 27-34, Vol. 11, No. 1, 1987.

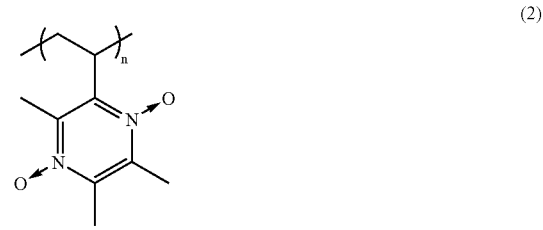

(2)

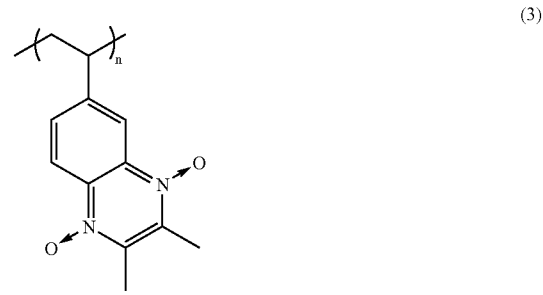

(3)

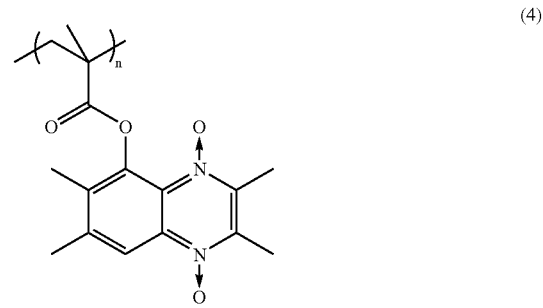

(4)

-continued

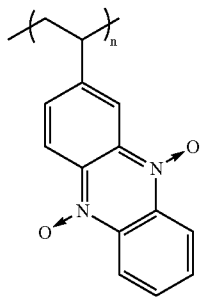
(5)

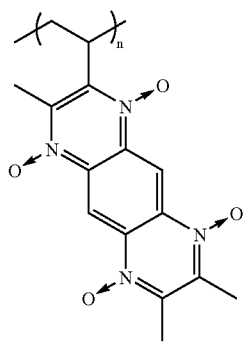
(6)

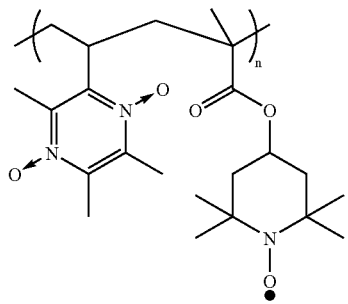
(7)

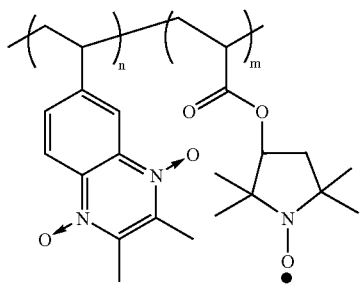
(8)

As described above, the compound having the diazine-N,N'-dioxide structure in the present invention may also have a structure coupled with the connector group A shown by the general formula (9). As specific examples of the compound, the compounds expressed by the chemical formula (10) and (11) below, however the present invention is not limited to these as long as the aforementioned main point is not exceeded.

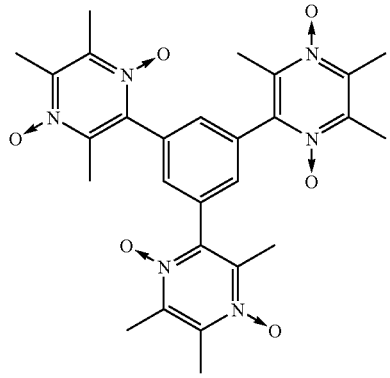
(10)

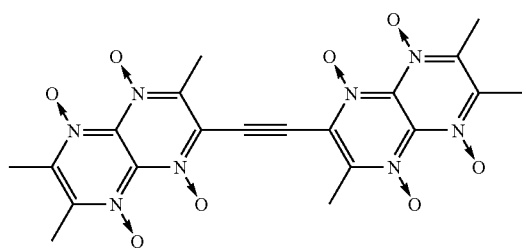
(11)

The other active material will be then described.

In a battery in the present invention containing a compound having the diazine-N,N'-dioxide structure as an active material of both positive and negative electrodes or either electrode, a compound having the diazine-N,N'-dioxide structure has characteristics of low mass density in comparison with metal oxide based active material, thereby having superior capacity density to be preferably used as the active electrode of the positive electrode. In such a battery in the present invention, when the compound having the diazine-N,N'-dioxide structure is used as the active material of one electrode, conventionally publicly known material listed below may be used as the active material used for the other electrode. The conventionally publicly known active material may also be mixed with the compound having the diazine-N,N'-dioxide structure to be used for both electrodes or either electrode as a composite active material.

When the compound having the diazine-N,N'-dioxide structure is used as an active material of a negative electrode, metal oxide particles, disulfide compound, conductive polymer and the like may be used as an active material of positive electrode. Lithium manganate such as $LiMnO_2$ and $Li_xMn_2O_4$ (0<x<2) or lithium manganate having a spinel structure, $MnO_2$, $LiCoO_2$, $LiNiO_2$, $Li_xV_2O_5$ (0<x<2) and so on are listed as metal oxide, dithioglycol, 2,5-dimercaptol-1,3,4-thiadiazole, S-triazine-2,4,6-trithiol and so on are listed as disulfide compound, and polyacetylene, polyphenylene, polyaniline, polypyrrole and so on are listed as conductive polymer. These positive electrode active material may be used in a single material of them or by combining two or more materials. Further, the conventionally publicly known active material and the compound having the diazine-N,N'-dioxide structure may be combined and used as a composite active material.

While, if the compound having the diazine-N,N'-dioxide structure is used as a positive electrode active material, graphite, amorphous carbon, lithium metal, lithium alloy, lithium ion occluded carbon, conductive polymer and so on are listed as a negative electrode active material and may be used in a single material of them or by combining two or more materials.

In addition, shape of the active material is not particularly limited, for instance, not only thin film shape, but also bulk shape, hardened up powder, fibriform shape, flaky shape and so on may be used for lithium metal and lithium alloy.

In the present invention, when an electrode containing the compound having the diazine-N,N,'-dioxide structure is formed, conductive auxiliary substance and ion conduction auxiliary substance may be mixed in order to decrease impedance. As conductive auxiliary substance, carbonaceous fine particle such as graphite, carbon black, acetylene black and so on and conductive polymer such as polyaniline, polypyrrole, polythiophene, polyacetylene, polyacene and so on are listed. As ion conduction auxiliary substance, gel electrolyte and solid electrolyte are listed.

In the present invention, binder may also be mixed in electrode material in order to strengthen binding between each constituent material in an electrode. As such a binder, resin binder such as polyvinylidene fluoride, vinylidene fluoride-hexafluoropropylene copolymer, vinylidene fluoride-tetrafluoride-tetrafluoroethylene copolymer, styrene-butadien copolymer rubber, polytetrafluoroethylene, polypropylene, polyethylene, polyimide and so on are listed.

In the present invention, catalyst for promoting redox reaction may also be mixed into the electrode material in order to smoothly perform electrode reaction. As such a catalyst, conductive polymer such as polyaniline, polypyrrole, polythiophene, polyacetylene, polyacene, basic compound such as pyridine derivative, pyrrolidone derivative, benzimidazole derivative, benzothiazole derivative, acridine derivative, and metal ion complex and so on are listed.

In the present invention, metal foil and metal plate such as nickel, aluminum, copper, gold, silver, aluminum alloy and stainless steel, mesh type electrode, carbon electrode and the like may be used as a negative electrode collector 1 and a positive electrode collector 6. Such a collector may also have catalytic effect and chemical bonding may be formed between the active material and the collector. An insulative packing 2 composed of plastic resin and so on may also be arranged between the negative electrode collector 1 and the positive electrode collector 6 for the purpose of preventing electrical contact between both collectors.

As a separator used for preventing contact between a positive electrode 5 and a negative electrode 3, a porous film and a nonwoven fabric may be used.

Then electrolyte will be described.

The electrolyte in the present invention takes charge of charge carrier-mediated transport between the electrodes and in general, desirably has ion conductivity of $1 \times 10^{-5}$ to $1 \times 10^{-1}$ S/cm at a room temperature. The electrolyte in the present invention, for instance, electrolytic solution formed by solving electrolytic salt in solvent may be used.

As such electrolytic salts, for instance, publicly known conventional material such as $LiPF_6$, $LiClO_4$, $LiBF_4$, $LiCF_3SO_3$, $Li(CF_3SO_2)_2N$, $Li(C_2F_5SO_2)_2N$, $Li(CF_3SO_2)_3C$, $Li(C_2F_5SO_2)_3C$ may be used.

As solvents of the electrolytic salts, organic solvent such as ethylene carbonate, propylene carbonate, dimethylcarbonate, diethylcarbonate, methylethylcarbonate, γ-butyrolactone, tetrahydrofuran, dioxolan, sulfolanc, dimethylformamide, dimethylacetoamide, and N-methyl-2-pyrrolidone may be used. In addition, in the present invention, these solvents may be used in a single kind of material or as a mixed solvent of two or more kinds of materials.

In the present invention, polymer electrolyte may also be used. The polymer electrolyte may be used in a gel state where electrolytic solution is contained in a polymer compound or the polymer compound itself may be used as a solid electrolyte without any change.

As such a polymer compound, vinylidene fluoride based polymer compound such as polyvinylidene fluoride, vinylidene fluoride-ethylene copolymer, vinylidene fluoride-monofluoroethylene copolymer, vinylidene fluoride-trifluoroethylene copolymer, vinylidene fluoride-hexafluoropropylene copolymer, vinylidene fluoride-hexafluoropropylene-tetrafluoroethylene tertial copolymer; acrylonitrile based polymer compound such as acrylonitrile-methylmethacrylate copolymer, acrylonitrile-methylmethacrylate copolymer, acrilonitrile-ethylmethacrylate copolymer, acrilonitrile-methylacrylate copolymer, acrylonitrile-ethylacrylate copolymer, acrylonitrile-methacryl acid copolymer, acrylonitrile-acryl acid copolymer, and acrylonitrile-vinylacetate copolymer, polyethylene oxide, ethylene oxide-propylene oxide copolymer, and acrylate ester thereof as well as methacrylate ester thereof and so on are listed, and these maybe used in a single kind of material or by combining two or more kinds of materials.

In the present invention, inorganic solid electrolyte may also be used. As the inorganic solid electrolyte, $CaF_2$, $AgI$, $LiF$, $\beta$ alumina, glass material and so on are listed When taking into consideration of the level of ion conductivity, electrolytic solution and gel electrolyte are preferable as an electrolyte of a battery in the present invention, particularly the electrolytic solution is preferable. When the compound having the diazine-N,N'-dioxide structure which has low solubility into the electrolytic solution is used as an active material, the electrolytic solution is preferably used as the electrolyte. While, when the compound having the diazine-N,N'-dioxide structure which has relatively high solubility into the electrolytic solution is used as an active material, solid electrolyte may be used, which the compound having the diazine-N,N'-dioxide structure is difficult to cause dissolution into the electrolyte.

Shape and appearance of the battery in the present invention is not particularly limited, and publicly known conventional battery may be adopted. Namely, as shapes of such battery in the present invention, for instance, products in which an electrode laminated product or a rolled product is sealed with a metal case, a resin case, or a laminated film and so on comprising metal foil such as aluminum foil and synthesis resin film may be listed. As the appearance of the battery, a cylinder type, a rectangular type, a coin type, a sheet type and so on are listed.

In the present invention, forms of lamination of the positive electrode and the negative electrode are not particularly limited, and they may be formed through a given laminating method. For instance, a multilayer laminated body, a form of combining bodies laminated on both surfaces of a collector, and a form of rolling the same may be used.

In the present invention, a manufacturing method of the electrode and the battery is particularly limited, and the publicly known conventional method may be adopted.

As the manufacturing method of the electrode, for instance, a method in which a solvent is added to constituent material of the electrode to form a slurry state and followed by applying the same on an electrode collector, a method in which a binder resin is added to the constituent material of the electrode and followed by putting pressure upon the material to harden up, a method in which the constituent material of the electrode is subjected to heat to sinter, and the like are listed.

The manufacturing method of the battery may comprise laminating the prepared electrode with an electrode of opposite pole via a separator, further rolling the laminated product, wrapping up the rolled product with an outer package, followed by sealing by injecting an electrolytic solution.

Also instead of the above, the manufacturing method of the battery may comprise laminating the prepared electrode with an electrode of opposite pole via a separator, wrapping up the laminated product with an outer package, followed by sealing by injecting an electrolytic solution.

In addition, during manufacturing the battery in the present invention, the compound having the diazine-N,N'-dioxide structure may be used without any change, or a compound capable of being converted through an electrode reaction into the diazine-N,N'-dioxide structure, that is a compound in which diazine-N,N'-dioxide ring of the diazine-N,N'-dioxide structure has a molecular structure of the compound (I), (II), (IV), or (V) shown by the reaction formula (A), may be used

EXAMPLES

The present invention will be described more specifically using examples, however, the present invention is not restricted to these examples.

Example 1

25 mg of polymer compound (weight-average molecular weight 5E4) having a diazine-N,N'-dioxide structure shown by the chemical formula (2) as a side chain, 200 mg of powder graphite, and 25 mg of polytetrafluoroethylene resin binder are measured and mixed in an agate mortar. Mixture obtained by dry blending for approx. 10 min. is subjected to a roller drawing by putting pressure to obtain a thin electrode plate of thickness of 215 μm. After drying the thin electrode plate in vacuum at a temperature of 80° C., the plate is punched out into a circle of diameter of 12 mm to obtain an electrode body.

Then, the obtained electrode body was soaked in an electrolytic solution to permeate the electrolytic solution into air gaps in the electrode body. Ethylenecarbonate/diethylcarbonate mixed solution (mixing ratio 3:7 (in volume)) containing $LiPF_6$ electrolytic salt of 1 mol/l was used for the electrolytic solution. The electrode body impregnated with the electrolytic solution was arranged on a positive electrode collector (aluminum foil) as a positive electrode, and a porous film separator impregnated with the electrolytic solution was laminated thereon in a similar manner. Lithium metal plate was further laminated as a negative electrode, and an insulative packing in a frame shape was placed before overlapping a negative electrode collector (copper foil). Pressure is applied on the obtained laminated product with a caulking machine to obtain a coin-shaped battery of an encapsulated type.

In the battery prepared as described above, charge was carried out at a constant electrical current of 0.1 mA using a positive electrode of the aluminum foil which forms the electrode containing polymer compound having the diazine-N,N'-dioxide structure shown by the chemical formula (2) as the side chain and a negative electrode of the copper foil attached with lithium, and just after voltage rose by 4.5V, discharge was carried out. Discharge electrical current was 0.1 mA same as when charging. As a result, a stationary part of the voltage was recognized around 4.0V, and it was confirmed to perform as a battery. Capacity per an active material was calculated to obtain 118 mAh/g.

Further, as to the obtained battery, variation in the voltage when the charge and discharge were repeated was measured. Consequently, even when the charge and discharge were repeated ten cycles, the stationary part of the voltage was recognized around 4.0V and the battery was confirmed to perform even as a secondary battery.

Comparative Example 1

An electrode was prepared in a same manner as example 1, except using 25 mg of powder graphite instead of polymer compound having a diazine-N,N'-dioxide structure shown by the chemical formula (2) used in the example 1 as a side chain, and a battery was prepared using an electrolyte, a separator, a positive electrode collector, and a negative electrode collector same as the example 1.

Using the battery prepared in the above-described manner, discharge was carried out in a same manner as the example 1. As the result, voltage decreases rapidly whereby the battery did not perform sufficiently as a battery.

When the charge was also tried on the battery by applying a constant current of 0.1 mA, the voltage instantaneously rose to obtain a voltage exceeding 4.5V. However, when the discharge was further carried out on the battery, the stationary part was not recognized on a voltage curve whereby the battery was confirmed not to perform as the secondary battery.

Comparative Example 2

An electrode was prepared in a same manner as example 1, except using 25 mg of $LiCoO_2$ instead of polymer compound having a diazine-N,N'-dioxide structure shown by the chemical formula (2) used for a positive electrode in the example 1 as a side chain, and a battery was prepared using an electrolyte, a separator, a positive electrode collector, and a negative electrode collector same as the example 1.

Using the battery prepared in the above-described manner, charge and discharge were carried out in a same manner as the example 1 and capacity per an active material was calculated to obtain 96 mAh/g.

Example 2

An electrode and a battery using the electrode were prepared in a same manner as example 1, except using polymer compound (weight-average molecular weight 4E4) having diazine-N,N'-dioxide structure expressed by a chemical formula (3) as a side chain instead of polymer compound having diazine-N,N'-dioxide structure shown by a chemical formula (2) used in the example 1 as a side chain.

Charge and discharge were carried out in a same manner as the example 1 on the obtained battery. As a result, a stationary part of voltage was recognized around 3.7V in the battery of the present example whereby the battery was confirmed to perform as a battery.

Further, variation in the voltage when the charge and discharge were repeated in a same manner as the example 1 was measured. Also in the battery of the present example, the charge and discharge repeated 10 cycles was possible and these batteries were confirmed to perform as a secondary battery. Capacity per an active material was calculated to obtain 103 mAh/g.

Example 3

An electrode and a battery using the electrode were prepared in a same manner as example 1, except respectively using polymer compound (weight-average molecular weight 4.5E4) having a diazine-N,N'-dioxide structure expressed by the chemical formula (4) as a side chain instead of polymer compound having the diazine-N,N'-dioxide structure shown by a chemical formula (2) used in the example 1 as a side chain.

Charge and discharge were carried out in a same manner as the example 1 on the obtained battery. As a result, a stationary part of voltage was recognized around 3.7V in the battery of the present example whereby the battery was confirmed to perform as a battery.

Further, variation in the voltage when the charge and discharge were repeated in a same manner as the example 1 was measured. Also in the battery of the present example, the charge and discharge repeated 10 cycles was possible and these batteries were confirmed to perform as a secondary battery. Capacity per an active material was calculated to obtain 101 mAh/g.

Example 4

An electrode and a battery using the electrode were prepared in a same manner as example 1, except respectively using polymer compound (weight-average molecular weight 5E4) having a diazine-N,N'-dioxide structure expressed by the chemical formula (5) as a side chain instead of polymer compound having the diazine-N,N'-dioxide structure shown by a chemical formula (2) used in the example 1 as a side chain.

Charge and discharge were carried out in a same manner as the example 1 on the obtained battery. As a result, a stationary part of voltage was recognized around 3.6V in the battery of the present example whereby the battery was confirmed to perform as a battery.

Further, variation in the voltage when the charge and discharge were repeated in a same manner as the example 1 was measured. Also in the battery of the present example, the charge and discharge repeated 10 cycles was possible and these batteries were confirmed to perform as a secondary battery. Capacity per an active material was calculated to obtain 115 mAh/g.

Example 5

An electrode and a battery using the electrode were prepared in a same manner as example 1, except respectively using polymer compound (weight-average molecular weight 42000) having a diazine-N,N,'-dioxide structure expressed by the chemical formula (6) as a side chain instead of polymer compound having the diazine-N,N'-dioxide structure shown by a chemical formula (2) used in the example 1 as a side chain.

Charge and discharge were carried out in a same manner as the example 1 on the obtained battery. As a result, a stationary part of voltage was recognized around 3.6V in the battery of the present example whereby the battery was confirmed to perform as a battery.

Further, variation in the voltage when the charge and discharge were repeated in a same manner as the example 1 was measured. Also in the battery of the present example, the charge and discharge repeated 10 cycles was possible and these batteries were confirmed to perform as a secondary battery. Capacity pet an active material was calculated to obtain 103 mAh/g.

Example 6

An electrode and a battery using the electrode were prepared in a same manner as example 1, except respectively using polymer compound (weight-average molecular weight 15000) having a diazine-N,N'-dioxide structure expressed by the chemical formula (7) as a side chain instead of polymer compound having the diazine-N,N'-dioxide structure shown by a chemical formula (2) used in the example 1 as a side chain.

Charge and discharge were carried out in a same manner as the example 1 on the obtained battery. As a result, a stationary part of voltage was recognized around 3.7V in the battery of the present example whereby the battery was confirmed to perform as a battery.

Further, variation in the voltage when the charge and discharge were repeated in a same manner as the example 1 was measured. Also in the battery of the present example, the charge and discharge repeated 10 cycles was possible and the battery were confirmed to perform as a secondary battery. Capacity per an active material was calculated to obtain 120 mAh/g.

Example 7

An electrode and a battery using the electrode were prepared in a same manner as example 1, except respectively using polymer compound (weight-average molecular weight 18000) having a diazine-N,N'-dioxide structure expressed by the chemical formula (8) as a side chain instead of polymer compound having the diazine-N,N'-dioxide structure shown by a chemical formula (2) used in the example 1 as a side chain.

Charge and discharge were carried out in a same manner as the example 1 on the obtained battery. As a result, a stationary part of voltage was recognized around 3.5V in the battery of the present example whereby the battery was confirmed to perform as a battery.

Further, variation in the voltage when the charge and discharge were repeated in a same manner as the example 1 was measured. Also in the battery of the present example, the charge and discharge repeated 10 cycles was possible and the battery was confirmed to perform as a secondary battery. Capacity per an active material was calculated to obtain 117 mAh/g.

Example 8

An electrode and a battery using the electrode were prepared in a same manner as example 1, except using a compound having a diazine-N,N'-dioxide structure expressed by the chemical formula (10) instead of a polymer compound having the diazine-N,N'-dioxide structure shown by a chemical formula (2) used in the example 1 as a side chain.

Charge and discharge were carried out in a same manner as the example 1 on the obtained battery. As a result, a stationary part of voltage was recognized around 3.8V whereby the battery was confirmed to perform as a battery.

Further, variation in the voltage when the charge and discharge were repeated in a same manner as the example 1 was measured. The charge and discharge repeated 10 cycles was possible and the battery were confirmed to perform as a secondary battery. Capacity per an active material was calculated to obtain 139 mAh/g.

Example 9

An electrode and a battery using the electrode were prepared in a same manner as example 1, except using a compound having a diazine-N,N'-dioxide structure expressed by the chemical formula (11) instead of a polymer compound having the diazine-N,N'-dioxide structure shown by a chemical formula (2) used in the example 1 as a side chain.

Charge and discharge were carried out in a same manner as the example 1 on the obtained battery. As a result, a stationary part of voltage was recognized around 3.6V whereby the battery was confirmed to perform as a battery.

Further, variation in the voltage when the charge and discharge were repeated in a same manner as the example 1 was measured. The charge and discharge repeated 10 cycles was possible and the battery were confirmed to perform as a secondary battery. Capacity per an active material was calculated to obtain 198 mAh/g.

INDUSTRIAL APPLICABILITY

According to the present invention, a battery which is high in capacity density and superior in stability of charge and discharge can be obtained by containing a compound having a specific diazine-N,N'-dioxide structure as an active material of a positive electrode and a negative electrode, or either electrode in a battery comprising at least a positive electrode, a negative electrode, and an electrolyte as constituent elements.

What is claimed is:

1. An electrode active material including a compound having a diazine-N,N'-dioxide structure, the electrode active material comprising:
    an oligomer or polymer compound containing in a side chain at least one monovalent group with one bond in a ring of the diazine-N,N'-dioxide structure shown by a general formula (1) described below,

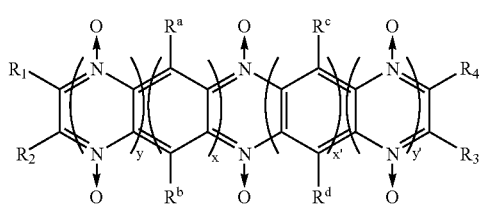

where x, y, x' and y' independently show integer numbers of 0 or more respectively, the order of condensation of diazine rings and benzene rings may be alternate or random, one of substituents $R_1$, $R_2$, $R_3$, $R_4$, $R_a$, $R_b$, $R_c$, and $R_d$ shows at least one monovalent group having the one bond and the other substituents independently show hydrogen atom, halogen atom, hydroxyl group, nitro group, nitroso group, cyano group, carboxyl group, substituted or unsubstituted alkyl group, substituted or unsubstituted alkenyl group, substituted or unsubstituted cycloalkyl group, substituted or unsubstituted aromatic hydrocarbon group, substituted or unsubstituted heteroaromatic group, substituted or unsubstituted aralkyl group, substituted or unsubstituted amino group, substituted or unsubstituted alkoxy group, substituted or unsubstituted allyloxy group, substituted or unsubstituted alkoxycarbonyl group, substituted or unsubstituted allyloxycarbonyl group, substituted or unsubstituted acyl group, or substituted or unsubstituted acyloxy group, $R_a$ on each benzene ring is same or different and $R_b$ on each benzene ring is same or different if x is 2 or more, and $R_c$ on each benzene ring is same or different and $R_d$ on each benzene ring is same or different if x' is 2 or more,
    wherein the molecular weight of the polymer compound is in a range of approximately 1000 to 500000.

2. An electrode active material as claimed in claim 1, wherein at least one atom of the substituent comprises a sulfur atom, silicon atom, phosphor atom or boron atom.

3. An electrode active material as claimed in claim 1, wherein the substituents form a ring structure.

4. An electrode active material as claimed in claim 1, wherein the compound is substantially insoluble into an electrolytic solution.

5. An electrode active material as claimed in claim 1, wherein molecular weight of the oligomer compound is in a range of approx. 200 to 1000.

6. An electrode active material as claimed in claim 1, wherein the oligomer or polymer compound comprises a copolymer.

7. An electrode active material comprising:
    a compound which has a diazine-N,N'-dioxide structure shown by a general formula (1) described below and which has a structure where the diazine-N,N'-dioxide structure is coupled by a connector group A shown by a general formula (9) described below,

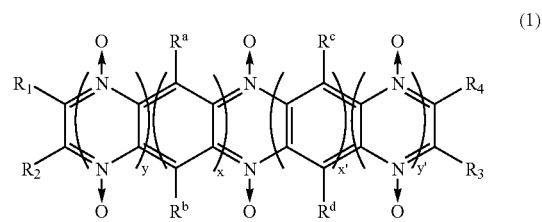

where x, y, x' and y' independently show integer numbers of 0 or more respectively, the order of condensation of diazine rings and benzene rings may be alternate or random, one of substituents $R_1$, $R_2$, $R_3$, $R_4$, $R_a$, $R_b$, $R_c$, and $R_d$ shows at least one monovalent group having the one bond and the other substituents independently show hydrogen atom, halogen atom, hydroxyl group, nitro group, nitroso group, cyano group, carboxyl group, substituted or unsubstituted alkyl group, substituted or unsubstituted alkenyl group, substituted or unsubstituted cycloalkyl group, substituted or unsubstituted aromatic hydrocarbon group, substituted or unsubstituted heteroaromatic group, substituted or unsubstituted aralkyl group, substituted or unsubstituted amino group, substituted or unsubstituted alkoxy group, substituted or unsubstituted allyloxy group, substituted or unsubstituted alkoxycarbonyl group, substituted or unsubstituted allyloxycarbonyl group, substituted or unsubstituted acyl group, or substituted or unsubstituted acyloxy group, $R_a$ on each benzene ring is same or different and $R_b$ on each benzene ring is same or different if x is 2 or more, and $R_c$ on each benzene ring is same or different and $R_d$ on each benzene ring is same or different if x' is 2 or more,

where A is the connector group and shows a group having a single bond or unsaturated bond, B shows a monovalent group expressed by the general formula (1), and z shows an integer number of 2 or more,
    wherein at least one atom of the substituent comprises a sulfur atom, silicon atom, phosphor atom or boron atom.

8. An electrode active material as claimed in claim 7, wherein z is an integer number of 2 to 10, and the connector group A comprises a substituent of z valence substituting bonds for z hydrogens of an aromatic compound with carbon number of 5 to 14 or a divalent group including alkyne, in the general formula (9).

9. An electrode active material as claimed in claim 7, wherein the substituents form a ring structure.

10. An electrode active material as claimed in claim 7, wherein the compound is substantially insoluble into an electrolytic solution.

11. An electrode active material as claimed in claim 7, wherein said diazine-N,N'-dioxide structure shown by the general formula (1) meets a condition of x+y+x'+y'≦20.

12. An electrode active material as claimed in claim 7, further comprising:
a catalyst which promotes redox reaction.

13. An electrode including a compound having a diazine-N,N'-dioxide structure, the electrode comprising:
an oligomer or polymer compound containing in a side chain at least one monovalent group with one bond in a ring of the diazine-N,N'-dioxide structure shown by a general formula (1) described below as a reactant, a reaction product, or an intermediate product in at least discharge reaction in an electrode reaction,

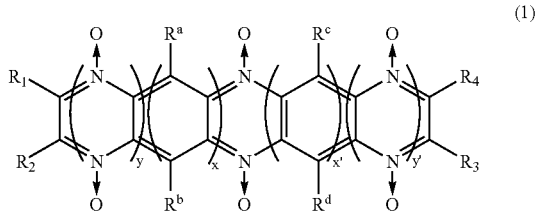

(1)

where x, y, x', and y' independently show integer numbers of 0 or more respectively, the order of condensation of diazine ring and benzene ring may be alternate or random, one of substituents $R_1$, $R_2$, $R_3$, $R_4$, $R_a$, $R_b$, $R_c$, and $R_d$ shows at least one monovalent group having the one bond and the other substituents independently show hydrogen atom, halogen atom, hydroxyl group, nitro group, nitroso group, cyano group, carboxyl group, substituted or unsubstituted alkyl group, substituted or unsubstituted alkenyl group, substituted or unsubstituted cycloalkyl group, substituted or unsubstituted aromatic hydrocarbon group, substituted or unsubstituted heteroaromatic group, substituted or unsubstituted aralkyl group, substituted or unsubstituted amino group, substituted or unsubstituted alkoxy group, substituted or unsubstituted allyloxy group, substituted or unsubstituted alkoxycarbonyl group, substituted or unsubstituted allyloxycarbonyl group, substituted or unsubstituted acyl group, or substituted or unsubstituted acyloxy group, $R_a$ on each benzene ring is same or different and $R_b$ on each benzene ring is same or different if x is 2 or more, and $R_c$ on each benzene ring is same or different and $R_d$ on each benzene ring is same or different if x' is 2 or more,
wherein the oligomer or polymer compound comprises a copolymer.

14. An electrode as claimed in claim 13, wherein at least one atom of the substituent comprises a sulfur atom, silicon atom, phosphor atom, or boron atom.

15. An electrode as claimed in claim 13, wherein the substituents form a ring structure.

16. An electrode as claimed in claim 13, wherein the compound is substantially insoluble into an electrolytic solution.

17. An electrode as claimed in claim 13, wherein a molecular weight of the oligomer compound is in a range of approx. 200 to 1000.

18. An electrode as claimed in claim 13, wherein a molecular weight of the polymer compound is in a range of approx. 1000 to 500000.

19. An electrode comprising:
a compound which has a diazine-N.N'-dioxide structure shown by a general formula (1) described below and which has a structure where the diazine-N.N'-dioxide structure is coupled by a connector group A shown by a general formula (9) described below as a reactant, a reaction product, or an intermediate product in at least discharge reaction in an electrode reaction,

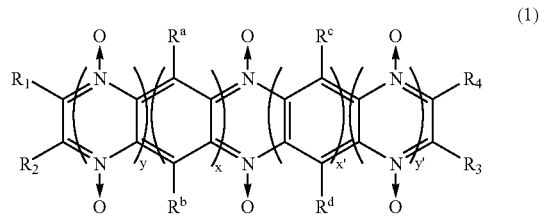

(1)

where x, y, x' and y' independently show integer numbers of 0 or more respectively, the order of condensation of diazine rings and benzene rings may be alternate or random, one of substituents $R_1$, $R_2$, $R_3$, $R_4$, $R_a$, $R_b$, $R_c$, and $R_d$ shows at least one monovalent group having the one bond and the other substituents independently show hydrogen atom, halogen atom, hydroxyl group, nitro group, nitroso group, cyano group, carboxyl group, substituted or unsubstituted alkyl group, substituted or unsubstituted alkenyl group, substituted or unsubstituted cycloalkyl group, substituted or unsubstituted aromatic hydrocarbon group, substituted or unsubstituted heteroaromatic group, substituted or unsubstituted aralkyl group, substituted or unsubstituted amino group, substituted or unsubstituted alkoxy group, substituted or unsubstituted allyloxy group, substituted or unsubstituted alkoxycarbonyl group, substituted or unsubstituted allyloxycarbonyl group, substituted or unsubstituted acyl group, or substituted or unsubstituted acyloxy group, $R_a$ on each benzene ring is same or different and $R_b$ on each benzene ring is same or different if x is 2 or more, and $R_c$ on each benzene ring is same or different and $R_d$ on each benzene ring is same or different if x' is 2 or more, $$A\text{-}(B)_z \quad (9)$$

where A is the connector group and shows a group having a single bond or unsaturated bond, B shows a monovalent group expressed by the general formula (1), and z shows an integer number of 2 or more,
wherein the substituents form a ring structure.

20. An electrode as claimed in claim 19, wherein z is an integer number of 2 to 10, and the connector group A comprises a substituent of z valence substituting bonds for z hydrogens of an aromatic compound with carbon number of 5 to 14 or a divalent group including alkyne, in the general formula (9).

21. An electrode as claimed in claim 19, wherein at least one atom of the substituent comprises a sulfur atom, silicon atom, phosphor atom, or boron atom.

22. An electrode as claimed in claim 19, wherein the compound is substantially insoluble into an electrolytic solution.

23. An electrode active material as claimed in claim 19, wherein said diazine-N,N'-dioxide structure shown by the general formula (1) meets a condition of x+y+x'+y'≦20.

24. An electrode active material as claimed in claim 19, further comprising:
a catalyst which promotes redox reaction.

25. A battery having as at least one electrode of a positive electrode or a negative electrode, an electrode including a compound having a diazine-N,N'-dioxide structure, the electrode comprising:
an oligomer or polymer compound containing in a side chain at least one monovalent group having one bond in a ring of the diazine-N,N'-dioxide structure shown by a general formula (1) described below as a reactant, a reaction product, or an intermediate product in at least discharge reaction in an electrode reaction,

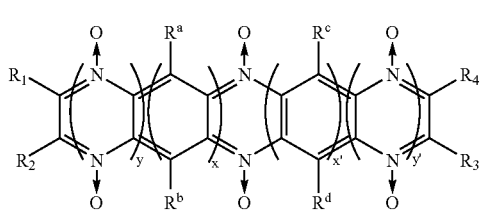
(1)

where x, y, x', and y' independently show integer numbers of 0 or more respectively, the order of condensation of diazine ring and benzene ring may be alternate or random, one of substituents $R_1$, $R_2$, $R_3$, $R_4$, $R_a$, $R_b$, $R_c$, and $R_d$ shows at least one monovalent group having the one bond and the other substituents independently show hydrogen atom, halogen atom, hydroxyl group, nitro group, nitroso group, cyano group, carboxyl group, substituted or unsubstituted alkyl group, substituted or unsubstituted alkenyl group, substituted or unsubstituted cycloalkyl group, substituted or unsubstituted aromatic hydrocarbon group, substituted or unsubstituted hecteroaromatic group, substituted or unsubstituted aralkyl group, substituted or unsubstituted amino group, substituted or unsubstituted alkoxy group, substituted or unsubstituted allyloxy group, substituted or unsubstituted alkoxycarbonyl group, substituted or unsubstituted allyloxycarbonyl group, substituted or unsubstituted acyl group, or substituted or unsubstituted acyloxy group, $R_a$ on each benzene ring is same or different and $R_b$ on each benzene ring is same or different if x is 2 or more, and $R_c$ on each benzene ring is same or different and $R_d$ on each benzene ring is same or different if x' is 2 or more.

26. A battery as claimed in claim 25, wherein one or more atoms of the substituent comprises a sulfur atom, silicon atom, phosphor atom, or boron atom.

27. A battery as claimed in claim 25, wherein the substituents form a ring structure.

28. A battery as claimed in claim 25, wherein the compound is substantially insoluble into an electrolytic solution.

29. A battery as claimed in claim 25, wherein a molecular weight of the oligomer compound is in a range of approx. 200 to 1000.

30. A battery as claimed in claim 25, wherein a molecular weight of the polymer compound is in a range of approx. 1000 to 500000.

31. A battery as claimed in claim 25, wherein the oligomer or polymer compound comprises a copolymer.

32. A battery having as at least one electrode of a positive electrode or a negative electrode, an electrode comprising:
a compound which has a diazine-N.N'-dioxide structure shown by a general formula (1) described below and which has a structure where the diazine-N.N'-dioxide structure is coupled by a connector group A shown by a general formula (9) described below as a reactant, a reaction product, or an intermediate product in at least discharge reaction in an electrode reaction,

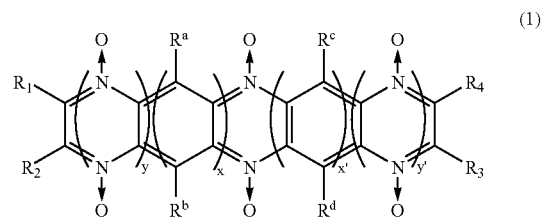
(1)

where x, y, x' and y' independently show integer numbers of 0 or more respectively, the order of condensation of diazine rings and benzene rings may be alternate or random, one of substituents $R_1$, $R_2$, $R_3$, $R_4$, $R_a$, $R_b$, $R_c$, and $R_d$ shows at least one monovalent group having the one bond and the other substituents independently show hydrogen atom, halogen atom, hydroxyl group, nitro group, nitroso group, cyano group, carboxyl group, substituted or unsubstituted alkyl group, substituted or unsubstituted alkenyl group, substituted or unsubstituted cycloalkyl group, substituted or unsubstituted aromatic hydrocarbon group, substituted or unsubstituted heteroaromatic group, substituted or unsubstituted aralkyl group, substituted or unsubstituted amino group, substituted or unsubstituted alkoxy group, substituted or unsubstituted allyloxy group, substituted or unsubstituted alkoxycarbonyl group, substituted or unsubstituted allyloxycarbonyl group, substituted or unsubstituted acyl group, or substituted or unsubstituted acyloxy group, $R_a$ on each benzene ring is same or different and $R_b$ on each benzene ring is same or different if x is 2 or more, and $R_c$ on each benzene ring is same or different and $R_d$ on each benzene ring is same or different if x' is 2 or more, A-(B)$_z$ (9)

where A is the connector group and shows a group having a single bond or unsaturated bond, B shows a monovalent group expressed by the general formula (1), and z shows an integer number of 2 or more,
wherein one or more atoms of the substituent comprises a sulfur atom, silicon atom, phosphor atom, or boron atom.

33. A battery as claimed in claim 32, wherein z is an integer number of 2 to 10, and the connector group A comprises a substituent of z valence substituting bonds for z hydrogens of an aromatic compound with carbon number of 5 to 14 or a divalent group including alkyne, in the general formula (9).

34. A battery as claimed in claim 32, wherein the substituents form a ring structure.

35. A battery as claimed in claim 32, wherein the compound is substantially insoluble into an electrolytic solution.

36. A battery a claimed in claim 32, wherein said diazine-N,N'-dioxide structure shown by the general formula (1) meets a condition of x+y+x'+y'≦20.

37. A battery as claimed in claim 32, further comprising:
a catalyst which promotes redox reaction.

* * * * *